United States Patent [19]

Hommeltoft et al.

[11] Patent Number: 5,457,258
[45] Date of Patent: Oct. 10, 1995

[54] RECOVERY OF SPENT ACID CATALYST FROM ALKYLATION OF HYDROCARBONS

[75] Inventors: Sven I. Hommeltoft, Hillerød; Claus J. H. Jacobsen, Copenhagen, both of Denmark

[73] Assignee: Haldor Topsøe A/S, Denmark

[21] Appl. No.: 271,117

[22] Filed: Jul. 6, 1994

[30] Foreign Application Priority Data

Jul. 6, 1993 [DK] Denmark .................................. 0813/93

[51] Int. Cl.$^6$ .............................. C07C 2/62; B01J 27/02
[52] U.S. Cl. ..................... 585/730; 585/719; 585/723; 585/724; 585/802
[58] Field of Search ................................. 585/719, 723, 585/724, 730, 802

[56] References Cited

U.S. PATENT DOCUMENTS

| | | | |
|---|---|---|---|
| 3,975,164 | 8/1976 | Brown, Jr. ............................ | 585/724 |
| 4,677,090 | 6/1987 | Fracasiu ............................... | 502/172 |
| 5,202,518 | 4/1993 | Del Rossi ............................. | 585/724 |

*Primary Examiner*—Asok Pal
*Attorney, Agent, or Firm*—Ostrolenk, Faber, Gerb & Soffen

[57] ABSTRACT

A method of recovery of acid catalyst from acid soluble oil being formed in a process for alkylation of hydrocarbons and containing valuable amounts of spent acid catalyst which method comprises, treating the acid soluble oil with hydrogen in the presence of a catalyst comprising one or more metals from Group VIII of the Periodic Table supported on an acid resistant carrier; and recycling the hydrotreated acid soluble oil to the alkylation process.

3 Claims, No Drawings

RECOVERY OF SPENT ACID CATALYST FROM ALKYLATION OF HYDROCARBONS

The present invention relates to certain improvements in the catalytic alkylation of aliphatic hydrocarbons in the presence of an acid catalyst, and, more particularly, to the recovery of such catalyst from acid soluble oil being formed during the processes.

Acid catalysed alkylation of aliphatic hydrocarbons with olefinic hydrocarbons is a well-known process for the preparation of high octane gasoline products. Alkylation of aliphatic hydrocarbons is generally accomplished in the liquid phase by reacting paraffins and olefins in the presence of a strong acid catalyst.

Conventionally used acids in industrial alkylation processes are hydrogen fluoride and sulphuric acid.

Utilization of fluorinated sulphonic acids as efficient alkylation catalysts in the alkylation of aliphatic hydrocarbons with olefins, is disclosed in European Patent Application No. 433,954, which by reference is enclosed herein. By the disclosed process, a process stream, including a hydrocarbon substrate and an olefinic alkylating agent, is reacted in contact with a fluorinated sulphonic acid catalyst in a fixed bed alkylation reactor containing polar contact material. On the contact material is established a reaction zone with the fluorinated sulphonic acid catalyst adsorbed within a confined area of the contact material. In the reaction zone, the process stream is converted at alkylating conditions to a product stream of alkylated hydrocarbons by catalysis of the fluorinated sulphonic acid adsorbed on the contact material.

During the alkylation reaction the acid catalyst and, consequently, the reaction zone moves as a well-defined band between the ends of the reactor due to interaction with the process stream flowing through and reacting in the zone.

During the migration of the acid catalyst on the contact material, the catalytic activity of the fluorinated sulphonic acid is substantially retained and the acid is still catalytic active, when the reaction zone reaches the reactor outlet.

Although it is possible to reuse the acid catalyst without recovery of the acid as it reaches the outlet end of the alkylation reactor by reversing the flow direction of the process stream introduced into the alkylation reactor, small amounts of the acid catalyst will continuously be absorbed in acid soluble oil being formed by side reactions during the process. The acid soluble oil adsorbs like the acid catalyst as a movable band on the support material adjacent to the reaction zone. It is, thus, possible to withdraw the acid soluble oil from the reactor, whenever the acid soluble oil band reaches one of the ends of the reactor.

Even if the acid soluble oil contains only small amounts of spent acid catalyst, it is desirable to recover the catalyst from the acid soluble oil in order to improve the economy of the alkylation process. Conventional methods, like distillation or extraction of the acid directly from the acid soluble oil, are not efficient because of strong interaction between the sulphonic acid and basic components in the acid soluble oil.

It is, therefore, a principal object of this invention to provide a process for the efficient recovery of acid catalyst from an alkylation process.

Accordingly, a broad embodiment of the invention is directed towards a method of recovery of acid catalyst from acid soluble oil being formed in a process for alkylation of hydrocarbons and containing valuable amounts of spent acid catalyst, which method comprises, treating the acid soluble oil with hydrogen in the presence of a catalyst comprising one or more metals from Group VIII of the Periodic Table supported on an acid resistant carrier; and recycling the hydrotreated acid soluble oil to the alkylation process.

The method according to the invention is, in particular, useful in the recovery of hydrogen fluoride and fluorinated sulphonic acid alkylation catalysts.

Hydrotreating catalysts for the recovery of those catalysts are preferably selected from platinum, palladium or mixtures thereof, supported on silica, zeolitic materials or activated carbon.

Hydrogenation of the acid soluble oil during recovery of spent acid catalyst from industrial alkylation units will preferably be carried out in stirred backmix reactors at a hydrogen partial pressure of between 1 and 150 bar and a temperature of 20°–300° C.

As an alternative hydrogenation may also be accomplished in continuously operated fixed bed reactors.

In the following more detailed description, the invention will be further illustrated by way of Examples describing some specific embodiments of the invention. In the Examples, acid soluble oil from the alkylation of isobutane with butene in the presence of trifluoromethanesulphonic acid ($CF_3SO_3H$), catalyst was hydrotreated under different conditions and the recovery rate of the catalyst measured.

Example 1

The catalyst composition and the reaction conditions are summarized in Table 1–3 below. A weighted amount of acid soluble oil was transferred to an autoclave and after the hydrogenation, the autoclave was cooled in acetone-dry ice prior to its opening. The autoclave was then washed thoroughly with water (5 times with approximately 100 ml.) to extract the acid and then the amount of the acid anion determined by ion chromatograph.

A substantial complete hydrogenation was obtained at 150° C. and 466 psi within 48 hrs.

As apparent from Table 2, mixed palladium and platinum catalysts are more active than catalyst containing these two metals separately. High hydrogenation rates using the mixed catalyst are obtained at 200° C. and 417 psi for 24 hrs. or at 150° C. and 511 psi for 72 hrs.

The influence of the partial pressure of hydrogen was tested by comparison of the results in Table 2 and Table 3, it is apparent that the reaction rate is not limited by diffusion of hydrogen in the reaction mixture at the relevant temperatures and pressures.

At a temperature of 200° C. and a hydrogen pressure of 699 psi for 24 hrs., it was possible to recover more than 93% of the acid initially present in the acid soluble oil.

TABLE 1

| Run # | 1 | 2 | 3 | 4 | 5 | 6 | 7 |
|---|---|---|---|---|---|---|---|
| g catalyst | 0.50 g | 0.50 g | 0.50 g | | 0.50 g | 0.50 | 0.50 |

TABLE 1-continued

| Run # | 1 | 2 | 3 | 4 | 5 | 6 | 7 |
|---|---|---|---|---|---|---|---|
| | 2% Pt/SiO$_2$ | 2% Pt/SiO$_2$ | 2% Pt/SiO$_2$ | | 2% Pt/SiO$_2$ | 2% Pt/SiO$_2$ | 2% Pt/SiO$_2$ |
| Acid soluble oil | 15 ml | 15 ml | 15 ml | | 15 ml | 15 ml | 15 ml |
| T/°C | 50 | 75 | 100 | | 125 | 90 | 90 |
| P/psi | 280 | 323 | 346 | | 369 | 338 | 337 |
| t/h | 18 | 18 | 18 | | 20 | 48 | 72 |
| Stirring | + | + | + | | + | + | + |
| Br.No. § | 34.9 | 37.9 | 24.5 | 24.5 | 11.4 | 27.4 | 27.1 |
| Acid + | 63% | 64.3% | 70.7% | 69.2% | 71.0% | 66.4% | 68.0% |
| % H$_2$O | 2.43 | 2.67 | 2.06 | 4.67 | 3.29 | 3.67 | 3.68 |

Acid soluble oil start Br. No. 46.3, CF$_3$SO$_3$H 61.3% by weight,

H$_2$O 2.20% by weight.

§: Bromine number.

+: Amount of CF$_3$SO$_3$H in hydrotreated acid soluble oil.

TABLE 2

| Run # | 8 | 9 | 10 | 11 | 12 | 13 | 14 |
|---|---|---|---|---|---|---|---|
| g catalyst | 0.50 g, 0.8% Pd, 0.2% Pt /SiO$_2$ | 0.50 g, 0.8% Pd, 0.2% Pt /SiO$_2$ | 0.50 g, 0.8% Pd, 0.2% Pt /SiO$_2$ | 0.50 g, 0.8% Pd, 0.2% Pt /SiO$_2$ | 0.50 g, 0.8% Pd, 0.2% Pt /SiO$_2$ | 0.50, 0.8% Pd, 0.2% Pt /SiO$_2$ | 0.50, 0.8% Pd, 0.2% Pt |
| Acid soluble oil | 15 ml | 15 ml | 15 ml | 15 ml | 15 ml | 15 ml | 20 ml/26-.65 g |
| T/°C | 80 | 125 | 150 | 75 | 200 | 150 | 200 |
| P/psi | 303 | 362 | 405 | 294 | 417 | 571 | 699 |
| t/h | 18 | 18 | 18 | 18 | 24 | 72 | 18 |
| Stirring | + | + | + | + | + | + | + |
| Br.No. § | 36.3 | 13.8 | 10.9 | 44.1 | 1.18 | 3.50 | |
| Acid + | 65.3% | 65.7% | 68.2% | 63.2% | 84.1% | 81.6% | |
| % H$_2$O | 3.05 | 3.65 | 3.77 | 2.76 | 3.21 | 6.02 | |

Acid soluble oil start Br. No. 46.3, CF$_3$SO$_3$H 61.3% by weight,

H$_2$O 2.20% by weight.

§: Bromine number.

+: Amount of CF$_3$SO$_3$H in hydrotreated acid soluble oil.

TABLE 3

| Run # | 15 | 16 |
|---|---|---|
| g catalyst | 0.50 g, 0.8% Pd, 0.2% Pt /SiO$_2$ | 0.50 g, 0.8% Pd, 0.2% Pt /SiO$_2$ |
| Acid soluble oil | 15 ml | 15 ml |
| T/°C | 125 | 100 |
| P/psi | 1132 | 1052 |
| t/h | 20 | 18 |
| Stirring | + | + |
| Br.No. § | 11.7 | 26.1 |
| Acid + | 63.8% | 68.2% |
| % H$_2$O | 4.30 | 3.18 |

Acid soluble oil start Br. No. 46.3, CF$_3$SO$_3$H 61.3% by weight,

H$_2$O 2.20% by weight.

§: Bromine number.

+: Amount of CF$_3$SO$_3$H in hydrotreated acid soluble oil.

Example 2

50 ml acid soluble oil was hydrogenated in a 2 l batch autoclave with an initial hydrogen pressure of 18 bar (at 25° C.). After 18 hrs. at 200° C., the autoclave was cooled. When the temperature had reached 45° C., the composition of the hydrocarbons in the gasphase was determined by gas chromatography showing the following composition:

| propane | 10% (w/w) |
| isobutane | 54% (w/w) |
| n-butane | 5% (w/w) |
| isopentane | 21% (w/w) |
| n-pentane | 1% (w/w) |
| C6+ | 9% (w/w) |

After further cooling, the autoclave was depressurised and the liquid decanted off. A gas-sample taken over the decanted product proved to contain the following organic components:

| propane | 5% (w/w) |
| isobutane | 36% (w/w) |
| n-butane | 4% (w/w) |
| isopentane | 24% (w/w) |
| n-pentane | 1% (w/w) |
| C6+ | 30% (w/w) |

A small amount of a lighter and somewhat volatile organic phase could be separated out from the heavier acid phase. GC-MS analysis of this light organic phase revealed a content of about 50% monocyclic alkanes (substituted cyclopentanes and cyclohexanes) and about 25% monoaromatics (substituted benzenes). 80% of the sample had a boiling point below about 150° C. and only about 5% had a boiling point above 200° C.

The acid phase contained about 15% organic material.

In order to test the catalytic activity of the recovered acid, a 10 ml sample of the acid phase was placed in a 100 ml reactor packed with silica gel (Merck 100, 0.2–0.5 mm particles) and a hydrocarbon feed stream containing 5% (w/w) 2-butene in isobutane (total flow: 150g/hr) was introduced into the reactor. 2-butene was converted quantitatively into alkylate. The composition of the alkylate, obtained thereby, was analyzed by gas chromatography. Based on the composition of several samples obtained at temperatures of between 0° C. and 30° C. the following octane numbers were calculated.

TABLE 4

| TEMPERATURE °C. | RON | MON |
|---|---|---|
| 30 | 93 | 91 |
| 25 | 94 | 92 |
| 20 | 95 | 92 |
| 15 | 96 | 93 |
| 10 | 97 | 94 |
| 5 | 97 | 94 |
| 0 | 98 | 95 |

We claim:

1. A method of recovery of trifluoromethanesulfonic acid catalyst from acid soluble oil being formed in a process for alkylation of hydrocarbons and containing valuable amounts of spent acid catalyst which method comprises, treating the acid soluble oil with hydrogen in the presence of a catalyst comprising one or more metals from Group VIII of the Periodic Table supported on an acid resistant carrier; and recycling the hydrotreated acid soluble oil to the alkylation process.

2. The method of claim 1, wherein the Group VIII metals are selected from platinum, palladium and mixtures thereof supported on a carrier selected from silica, zeolitic materials and activated carbon.

3. The method of claim 1, wherein the treatment with hydrogen is carried out at a hydrogen partial pressure of between 1 and 150 bar and at a temperature of between 20°–300° C.

* * * * *